United States Patent [19]

Lin

[11] Patent Number: 5,085,660
[45] Date of Patent: Feb. 4, 1992

[54] INNOVATIVE LOCKING PLATE SYSTEM

[76] Inventor: Kwan C. Lin, 45 Duncan St., Staten Island, N.Y. 10304

[21] Appl. No.: 615,390

[22] Filed: Nov. 19, 1990

[51] Int. Cl.$^5$ .............................................. A61F 5/04
[52] U.S. Cl. ..................................... 606/73; 606/72; 606/60; 606/69
[58] Field of Search ...................... 128/69; 606/60, 69, 606/70-73, 86, 101, 104, 61; 623/17; 433/172-174

[56] References Cited

U.S. PATENT DOCUMENTS

| | | | |
|---|---|---|---|
| 3,842,825 | 10/1974 | Wagner | 606/101 |
| 4,794,918 | 1/1989 | Wolter | 606/72 |
| 4,964,403 | 10/1990 | Karas et al. | 606/60 |

FOREIGN PATENT DOCUMENTS

| | | | |
|---|---|---|---|
| 742618 | 3/1933 | France | 606/69 |
| 782462 | 6/1935 | France | 606/73 |
| 2254298 | 7/1975 | France | 606/73 |

*Primary Examiner*—Richard J. Apley
*Assistant Examiner*—Linda C. M. Dvorak
*Attorney, Agent, or Firm*—Bacon & Thomas

[57] ABSTRACT

A locking plate system has multiple locking pins, each with one end formed as a screw to lock in the pending fixation bones or vertebral tubercles, with another end defining rectangular or similarly shaped locking post having a threaded locking end. Near the locking post end, there is formed a stopping protrusion. A plate defines multiple locking bores disposed at one side to be placed over the locking post end until the plate reaches the stopping protrusion on the locking pin. The plate defines multiple threaded screwing bores near the other side to receive locking pin screw. Multiple locking devices fix the side of the plate having locking bores to the locking post end of its locking pins. Multiple screwing pins each have one end formed as a pin to be used for penetrating the the threaded screwing bore to lock into the bone or the vertebral tubercle. Another end which forms a head is for holding against the threaded screwing bore of the plate. Threads are provided near the head for the screwing pins to be screwed within the threaded screwing bore of the plate.

3 Claims, 1 Drawing Sheet

INNOVATIVE LOCKING PLATE SYSTEM

BACKGROUND OF THE INVENTION

This invention relates to an innovative locking plate system, and more particularly to such a locking plate system for the locking of bones or vertebral tubercles.

Essential, the prior art locking plate system involves the placement of a plate on two adjacent mobile bone surfaces and then, through a hole defined by the plate, a screw is inserted and used to lock the plate on those bone surfaces. In the prior art, the plate is vulnerable to loosening. Further, the screw is loosened as well, since the contacting surface between plate and bone is not totally matched (due to the different curvatures involved) and the plate is pressed against the bone by the head of the screw. Plates, used to fix the vertebral tubercles, such as: I-plate [See Hansen A, Yuan, MD, et al. Spine, 13(3), 278, 1988]; C.A.S.F. Plate by ArcoMed; A. O. Plate & Screw by Synthes; and Swiss and B. G. Spinal Plate by Howmedica U.K., all use screws to press the plates tightly against vertebral tubercles, but do not combine the screw, the plate and the vertebral tubercles into an integral unit. Therefore, these plates are exposed to the same defect of being easily loosened up as the aforesaid plate systems. In addition, the traditional vertebral tubercles fixation system, such as a Kaneda device, uses a rod and nut to link each vertebral tubercle. When such a system is applied in an operation, the rod is required to shuttle through two screws on the Kaneda plates, resulting in operating difficulties. Furthermore, preplacement of the exterior nut requires the surgical opening to be widened and requires more operating time, leading to more operative hemorrhage. Finally, a Kaneda device is not useable for the ordinary bone fixation.

SUMMARY OF THE INVENTION

Accordingly, it is an object of the present invention to provide a locking plate system capable of firmly fixing bones or vertebral tubercles.

Another object of the present invention is to provide a locking plate system comprising a plate, locking pins, locking devices and threaded screwing pins.

With the above objects in view, the locking plate system according to the present invention comprises multiple locking pins, each with one end formed with a screw thread used to lock in the bones or vertebral tubercles, another end defining a rectangular or similarly shaped post having a threaded locking end, and near the locking post end there is formed a stopping protrusion; a plate defining multiple locking bores which are disposed near one side that are adapted to be placed over the locking post end until reaching said stopping protrusion on the locking pins and multiple threaded screwing bores near another side adapted to receive screws; multiple locking devices to fix the side of the plate having the locking bores to the locking post end of said locking pins; and multiple screwing pins, each with one end adapted to be used for penetrating the threaded screwing bores of the plate to lock the plate in position onto the bone or the vertebral tubercle, while the other end of the screwing pin defines a head used for holding against the threaded screwing bore of said plate. Threads are provided near the head for the screwing pins which are to be screwed into the threaded screwing bores of said plate.

BRIEF DESCRIPTION OF THE DRAWING

The present invention will become more readily apparent from the following description taken in conjunction with the accompanying drawing, but in no way limits the scope of the present invention, wherein.

DETAILED DESCRIPTION OF THE PREFERRED EMBODIMENT

Figure 1:
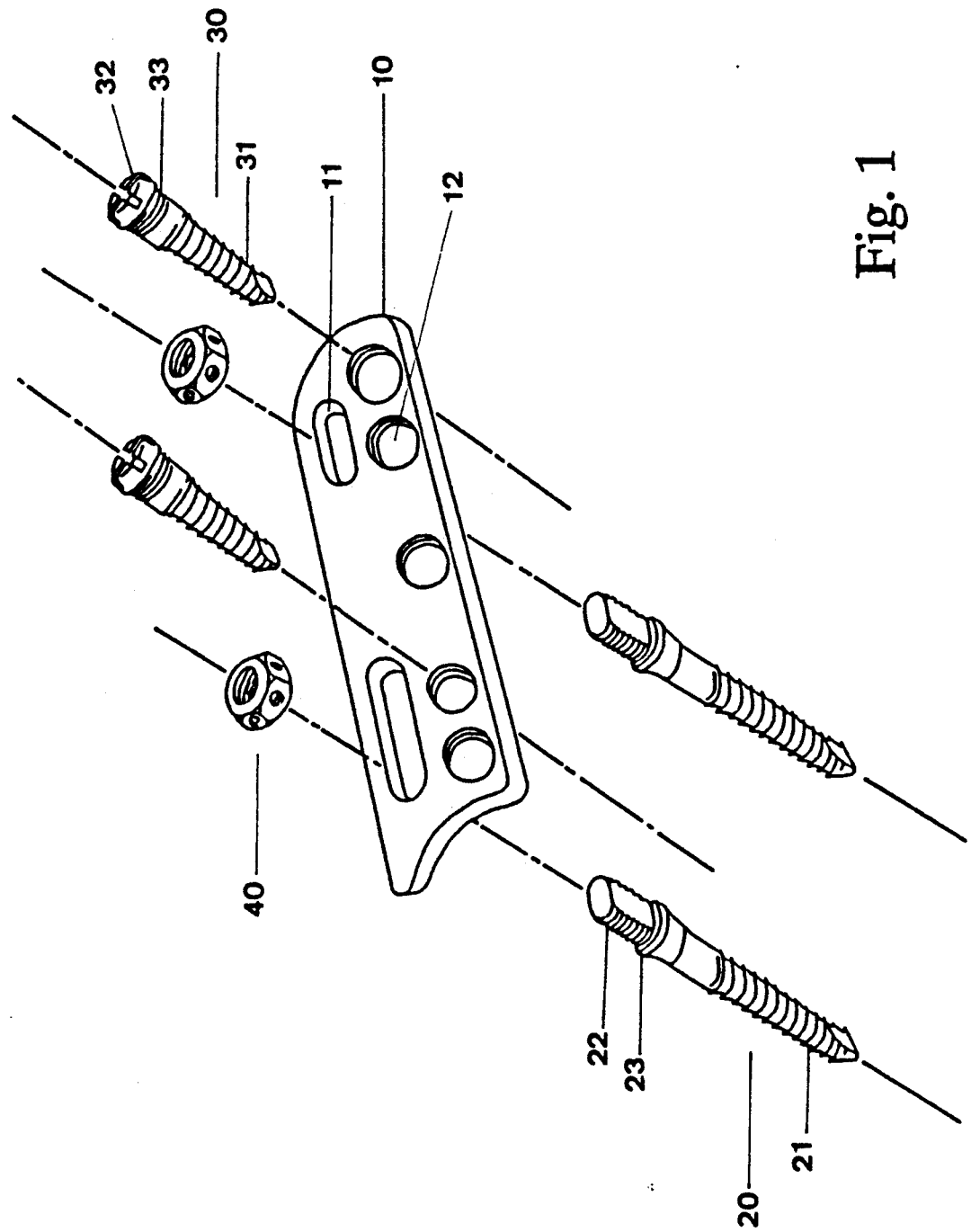
FIG. 1 is an exploded, perspective view illustrating the locking plate system constructed according to the preferred embodiment of the present invention.

The present invention provides an innovative locking plate system, which comprises multiple locking pins 20 each with one end defining a screw 21 for insertion into the pending fixation bones or vertebral tubercles. Another end defines a rectangular or similarly shaped post having a threaded locking end 22. Near the locking end 22 there is formed a stopping protrusion 23. A plate 10 defining multiple locking bores 11 disposed near one side is adapted to be placed over the locking end 22 until it reaches said stopping protrusion 23 on said locking pin 20. Multiple threaded screwing bores 12 are defined by plate 10 near another side to receive threaded screwing pins 30. Multiple locking devices 40 engage locking ends 22 to fix the side of the plate 10 having locking bores 11 onto those locking ends 22 of said locking pins 20. Multiple screwing pins 30 each have one end 31 used for penetrating the threaded screwing bore 12 to lock in position onto the bone or the vertebral tubercle. The other end forms a head 32 used for holding against the threaded screwing bores 12 of said plate 10. Threads 33 are provided near the head 32 to be screwed within the threaded screwing bores 12 of said plate 10.

Any generally accepted and applicable osteological materials, such as metal which can be inserted within human body, e.g. s.s. 316 LVM, Ti-6-4 as well as cobalt and nickel alloy materials all can be used for the making elements of the present invention. Said plate 10 of the present invention may optionally be a curved plate, formed depending on the shape of the bone (vertebral tubercle) to be fixed. In this case each of the multiple locking bores 11 is preferably shaped in a similar rectangle, having four corners wherein the pair of short sides of said rectangular bore have the shape of an arc. Further, the concave bottom of said locking bore 11 shall be formed to accommodate precisely the stopping protrusion 23 of said pins 20.

The top end 22 of each of said locking pins 20 defines a rectangular or similarly shaped post. The similarity referred to here requires corners and a pair of short sides to be in arc shape similar to the aforesaid locking bores 11. By penetrating through said locking bores 11 of the aforesaid plate 10, said post 22 is confined by such locking bores 11, that is, the pin 20 will stay firmly, and be free of any turning so as to prevent loosening.

Any kind of applicable locking device 40 can be used for the locking system of the present invention. Namely, the nut for single locking or for double locking as even a locking screw can be added to reinforce the fixation effect.

The threaded screwing pin 30 by threads 33 near its top end is directly coupled with those threads on the threaded screwing bore 12 of said plate 10, thus yielding a very excellent fixation. Further, a selflocking screw can be used to stress its locking function.

It is preferred to form cross acute angles with the axes of said locking pins 20 and screwing pins 30 when locking into the bone or vertebral tubercles. More particularly, it is preferred that the axes point in the direction of the center of said bones or vertebral tubercles.

The present invention creates for the first method of locking into the bones (or vertebral tubercles) with a locking pin top which is then fixed with its stopping protrusion and fixing device (instead of compression) onto the plate 10 whereby the plate, locking pins and bones (vertebral tubercles) are integrated as a whole unit. This eliminates the traditional method of locking by using the pins to compress plate tightly against the bones (or vertebral tubercles). In the present system the screwing pin 30 is also locked with its top into the bones (or vertebral tubercles) and is coupled to the plate 10 with threads 33 near pin top 32, thereby making bones (or vertebral tubercles), plate and screwing pin form an integrated unit. In FIG. 1 10 is the plate, 11 the similarly shaped rectangular locking bore, 12 the threaded screwing bore, 20 the locking pin, 21 the screw portion, 22 the locking end, 23 the stopping protrusion, 30 the screwing pin, 31 the pin portion, 32 the pin head, the threads and 40 the nut locker. The locking plate system uses screw portion 21 of locking pin 20 to lock it into the bone or vertebral tubercle as the locking bore 11 of plate 10 is placed over the locking end 22 of locking pin 20 and reaches stopping protrusion 23 of locking pin 20 for fixation. Further, lock pin 30 penetrates screwing bore 12 into the bone or vertebral tubercle and its thread 33 is coupled with threads from threaded screwing bore 12 to achieve the purpose of reinforcing the locking effect.

What is claimed is:

1. A locking plate system for locking together adjacent bones or vertebral tubercles comprising:
   a) a plurality of locking pins, each locking pin having a threaded end adapted to be threaded into a bone or vertebral tubercle, a locking end and a stopping protrusion located between the threaded end and locking end;
   b) a plate defining a first plurality of locking bores adapted to non-rotatably accept the locking ends of the locking pins such that the locking ends extend through the plate thereby enabling a side of the plate facing the bone or vertebral tubercle to rest on the stopping protrusions to prevent movement of the plate toward a bone or vertebral tubercle, the plate further defining a plurality of threaded bores;
   c) a plurality of screwing pins, each screwing pin having a first threaded portion adapted to be threaded into a bone or vertebral tubercle and a second threaded portion adapted to be threaded into a threaded bore of the plate; and,
   d) locking devices engageable with the locking ends of the locking pins after they have passed through the locking bores of the plate to hold the plate assembled to the locking pins.

2. A locking system according to claim 1, wherein said plate is a curved plate.

3. A locking system according to claim 1, wherein both said locking pin and screwing pin point generally towards a center of a bone or vertebral tubercle to which they are threaded thus forming a cross acute angle.

* * * * *